US 8,417,008 B2

(12) United States Patent
Biermann et al.

(10) Patent No.: US 8,417,008 B2
(45) Date of Patent: Apr. 9, 2013

(54) METHOD FOR HIGHLIGHTING LOCAL CHARACTERISTICS IN ANATOMICAL VOLUME RENDERINGS OF VESSEL STRUCTURES AND COMPUTER SYSTEM FOR CARRYING OUT THIS METHOD

(75) Inventors: Christina Biermann, Hausen (DE); Fernando Vega-Higuera, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 332 days.

(21) Appl. No.: 12/916,756

(22) Filed: Nov. 1, 2010

(65) Prior Publication Data
US 2011/0103667 A1 May 5, 2011

(30) Foreign Application Priority Data
Nov. 2, 2009 (DE) .................. 10 2009 052 315

(51) Int. Cl.
*G06K 9/00* (2006.01)
(52) U.S. Cl.
USPC ............................... 382/131; 382/284; 378/4
(58) Field of Classification Search .................. None
See application file for complete search history.

(56) References Cited

U.S. PATENT DOCUMENTS

| | | | |
|---|---|---|---|
| 7,715,608 B2 | 5/2010 | Vaz | |
| 2006/0056691 A1 | 3/2006 | Vaz | |
| 2008/0144903 A1* | 6/2008 | Wang et al. | 382/130 |
| 2008/0273784 A1 | 11/2008 | Pfister | |
| 2009/0028287 A1 | 1/2009 | Krauss | |

FOREIGN PATENT DOCUMENTS

| | | |
|---|---|---|
| CA | 2365323 A1 | 6/2003 |
| DE | 102005036875 A1 | 5/2006 |
| DE | 102007027192 A1 | 12/2008 |

OTHER PUBLICATIONS

F. Vega-Higuera et al., "High Performance Volume Splatting for Visualization of Neurovascular Data" Proceedings of IEEE Visualization, Oct. 2005, 271-278; Others.
Kniss, J. et.al., Interactive Volume Rendering Using Multi-Dimensional Transfer Functions and Direct Manipulation Widgets, Proc. of IEEE Visualization 2001, 2001; Others; 2001.

(Continued)

*Primary Examiner* — Andrew W Johns
*Assistant Examiner* — Siamak Harandi
(74) *Attorney, Agent, or Firm* — Harness, Dickey & Pierce, P.L.C.

(57) ABSTRACT

A method is disclosed for highlighting local characteristics in anatomical volume renderings of vessel structures and a computer system is disclosed for carrying out this method. In at least one embodiment of the method, the method includes determining or receiving a volume of interest; generating or receiving at least one first tomographic volume data record in the volume of interest, having a rendered display of a vessel structure; generating or receiving at least one second volume data record, which is used as a mask for the first volume data record and has at least one characteristic vector with a minimum data width of 2 bit for each voxel; accepting at least one characteristic definition for at least one predefined position or predefined region of the mask or the first volume data record, which is at the same position, and encoding the at least one characteristic definition in at least one characteristic vector of the mask; and combined rendering of the first volume data record and the mask, wherein the mask translucently marks a defined surrounding area of the predefined position as a function of the characteristic vectors present there.

14 Claims, 6 Drawing Sheets

OTHER PUBLICATIONS

Viola, Ivan et.al., Importance-Driven Volume Rendering, IEEE Transactions on Visualization and Computer Graphics. vol. 11, Issue 4, 408-418,2005; Others; 2005.

Kniss J. et.al., Multi-Dimensional Transfer Functions for Interactive Volume Rendering, IEEE Transactions on Visualization and Computer Graphics, Jul.-Sep. 2002, vol. 8, No. 3, pp. 270-285; Others.

* cited by examiner

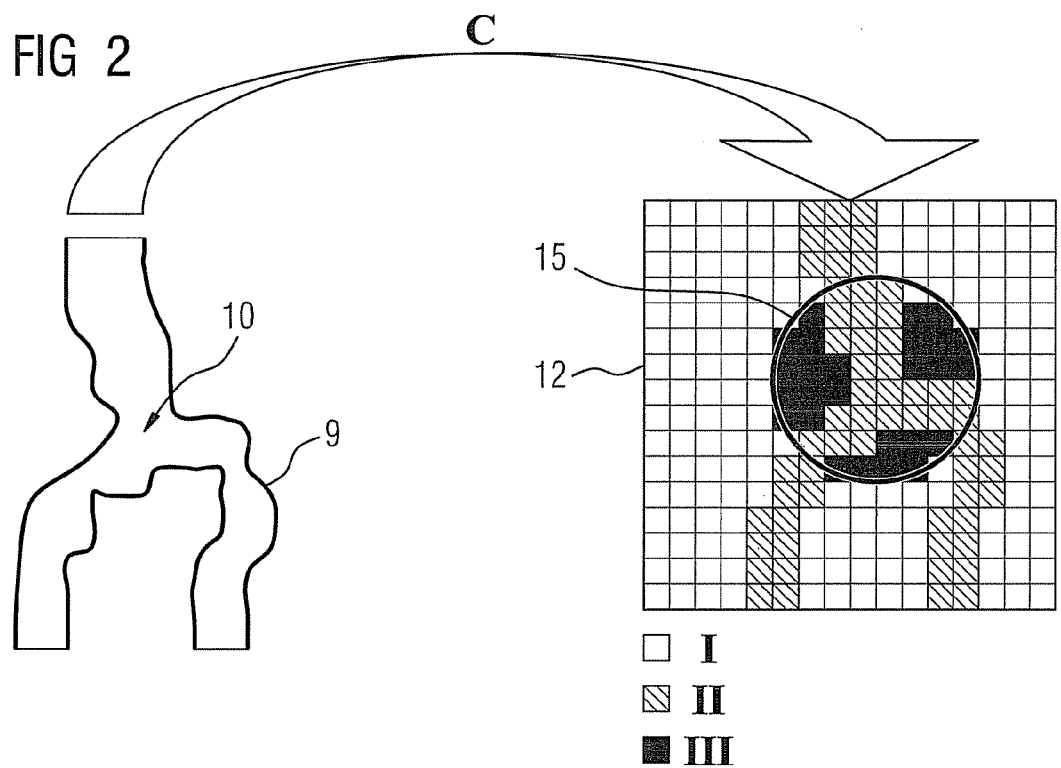
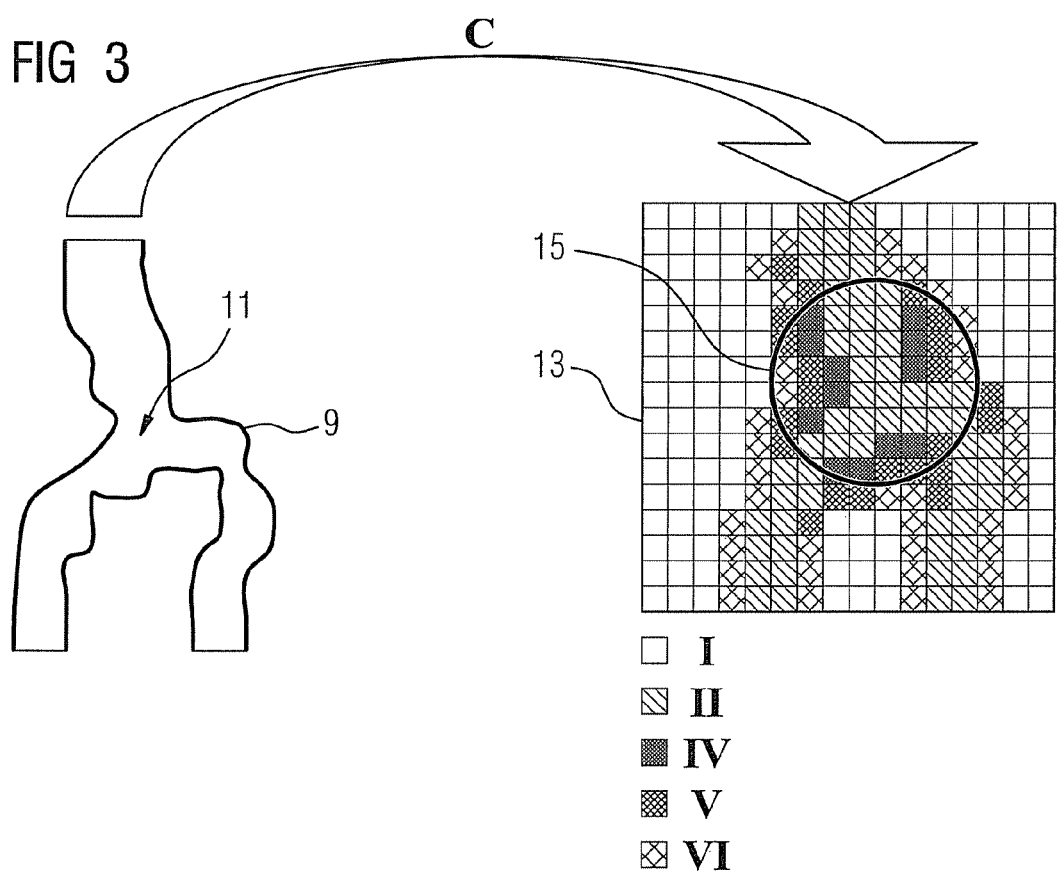

FIG 5
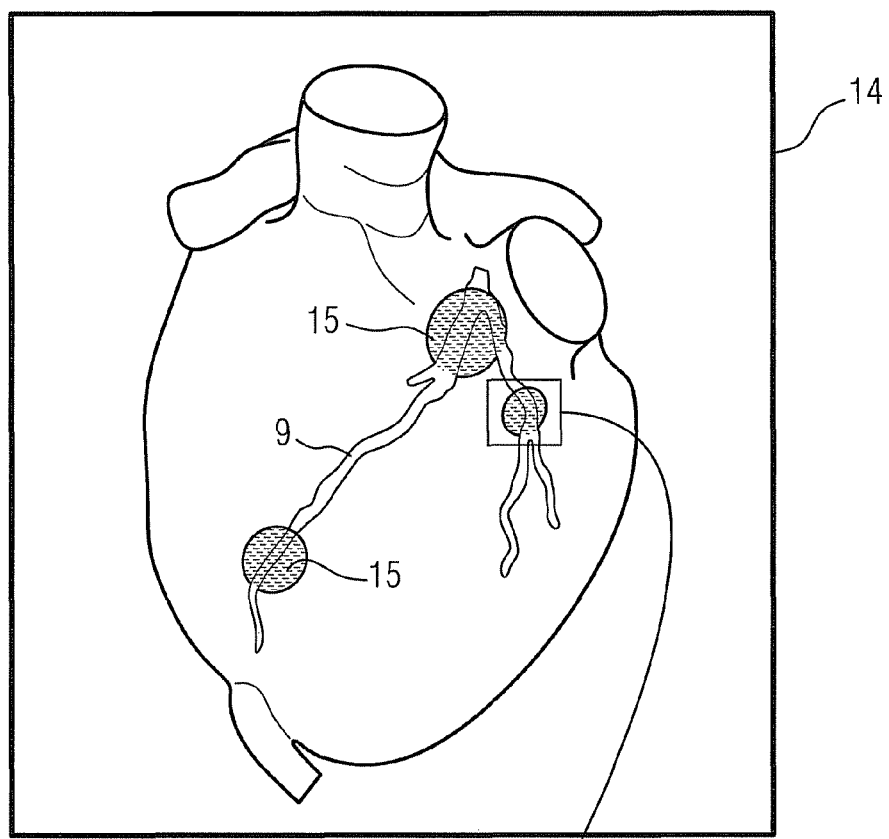
Detail A
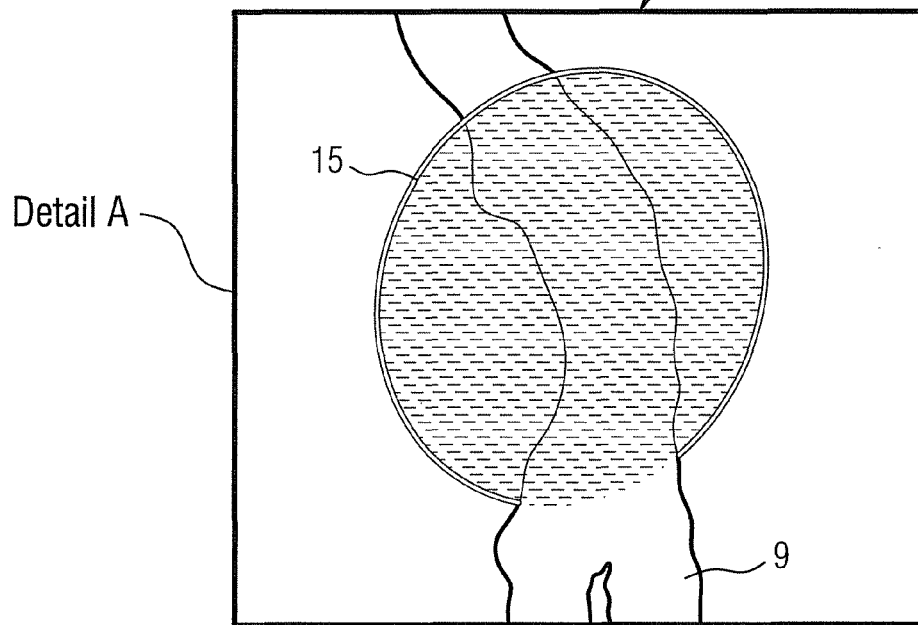

METHOD FOR HIGHLIGHTING LOCAL CHARACTERISTICS IN ANATOMICAL VOLUME RENDERINGS OF VESSEL STRUCTURES AND COMPUTER SYSTEM FOR CARRYING OUT THIS METHOD

PRIORITY STATEMENT

The present application hereby claims priority under 35 U.S.C. §119 on German patent application number DE 10 2009 052 315.4 filed Nov. 2, 2009, the entire contents of which are hereby incorporated herein by reference.

FIELD

At least one embodiment of the invention generally relates to a method for highlighting local characteristics in anatomical volume renderings of vessel structures, wherein, in a volume of interest (VOI), characteristic definitions, such as manually or automatically collected findings in respect of certain regions of the rendering, are intended to be emphasized and shown provided with additional information.

BACKGROUND

As a result of the diagnostic techniques that are becoming evermore specific and also of the examinations that are carried out at different locations because of this, it is becoming evermore frequently necessary to provide a multiplicity of items of diagnostic information from various locations to a multiplicity of diagnosis and treatment professionals. In principle, this was until now carried out by writing down findings in written-text form, with the respective treating medical practitioner having to read all ultimately irrelevant and relevant findings and to order them according to importance, and finally having to draw their own diagnostic and/or therapeutic conclusions from the collection of available external and their own information. An improvement in respect of the coordination of such quantities of information was achieved by modern telecommunications devices. Using these devices, information can now be exchanged without great time delay, with, for example, even complete CT renderings, provided with findings where necessary, being exchanged.

Known is the practice of labeling the findings, the probability thereof as well, where necessary, or other characteristics of lesions by using written markings (e.g. "flags" with reference lines to the examined position or lesion) when rendering three-dimensional vessel structures, more particularly when rendering coronary vessels, on the basis of CT or CTA recordings at positions that were examined by a medical practitioner or at positions that were assessed by an automated findings system.

SUMMARY

The inventors have discovered that this results in two significant problems. Firstly, the rendering becomes unclear as a result of a multiplicity of markings and labels, or the markings and labels cover essential anatomical structures. As a result of this, lesions that are still undiscovered may remain in the background solely as a result of the information relating to other, previously discovered lesions, and may ultimately not be taken into account during the examination. Secondly, it requires increased attention and concentration to actually read and take-in the information contained in written form in its entirety. This also makes it easy to overlook essential findings and indications during the observation. Overall, it is easy to lose track in the case of such markings.

At least one embodiment of the invention is directed to a marking system for vessel structures rendered in three dimensions, which renders to the observer a simplified and quicker overview over the sum of information that is added to a volume rendering of vessel structures.

Advantageous developments of the invention are the subject matter of dependent claims.

The inventors have identified that a significant problem in respect of rendering and transmitting findings data lies in the fact that most findings data is transmitted as text, and so the person receiving the information needs to concentrate hard to take-in this written information, which may even be written in different languages, in its entirety, to assign this information to the correct anatomical positions where necessary, and to order it correctly according to its relevance from the transmitted text. There is a need for an improved and less language or text dependent alternative for exchanging information, particularly when transmitting information and findings in a medical field where vessel renderings and the assessment thereof are relevant. A significant improvement in this information exchange can be obtained by virtue of the fact that the information to be transferred is not transferred in text form but in the form of transparent graphical markings, which are embodied here such that the relevant anatomical structure is depicted as unaltered as possible and, at the same time, the positions or regions of diagnostic relevance, for example lesions or stenoses, are marked by spherical graphical overlays. In the process, the markings should be embodied such that the observer can identify, from the embodiment and design, preferably the coloring, of the marking, what findings are represented thereby, from which source the respective assessment originates and what is the basis for the relevance of the assessment. Thus, once a person has studied the meaning of the graphical markings, this person can very quickly gain an overview over the respective findings situation when viewing a vessel rendering with corresponding graphical markings, which are the result of the findings originating from different external sources, without laboriously needing to read a multiplicity of long findings reports. At the same time, the actual anatomical structure may easily remain identifiable with such a transparent marking, and so there is nothing in the way of an individual assessment.

A technical embodiment of such a rendering according to at least one embodiment of the invention can use the possibilities of modern graphics cards in an optimum fashion by providing predefined image regions with predetermined transparent markings or transparent spheres using program modules of the graphics card.

In accordance with this basic idea illustrated above, in at least one embodiment the inventors propose a method for highlighting local characteristics in anatomical volume renderings of vessel structures, comprising:

determining or receiving a volume of interest (VOI), which comprises the following method steps:

generating or receiving at least one first tomographic volume data record in the VOI, having a rendered display of a vessel structure, generating or receiving at least one second volume data record, which is used as a mask for the first volume data record and has at least one characteristic vector with a minimum data width of 2 bit for each voxel, accepting at least one characteristic definition for at least one predefined position or predefined region of the mask or the first volume data record, which is at the same position, and encoding the at least one characteristic definition in at least one characteristic vector of the mask, combined rendering of the first volume data record and the mask, wherein the mask translucently marks a defined surrounding area of the predefined position as a function of the characteristic vectors present there.

At least one embodiment of the method can preferably be applied in conjunction with CT or CTA examinations (CT=computed tomography, CTA=computed tomography angiography), more particularly if the at least one first tomographic volume data record shows the coronary arteries in the heart of a patient.

In at least one embodiment of the proposed method, at least one entry of a characteristic definition can be a finding by a medical practitioner and/or a finding from an automated findings system. In particular, if the entered characteristic definitions originate from a computer aided diagnostic (CAD) system, then it is advantageous for a probability of the finding being correct to be specified as well in addition to the finding.

In order to grant an optimum and quick overview, it is particularly expedient for each characteristic definition to be assigned its own color and/or color intensity. In the process, each probability or each probability range for the presence of a finding can preferably be assigned its own color or its own color intensity.

Then again, it is also possible to assign their own color or to each user who enters a finding color range.

Each finding can likewise be assigned its own type of representation. Thus, for example, the finding indicating a stenosis can be assigned a spherical representation, which corresponds to a 3D rendering of a narrowing, or an aneurysm can be assigned a schematic representation of a vessel widening. Thus, self-explanatory, pictogram-like representations can be used, which require neither the observer having prior knowledge nor a legend being read.

Furthermore, masks can be created from at least two different sources with characteristic definitions and the at least two masks can be rendered together in conjunction with the first volume data record, or individually, depending on the observer's entry. This allows targeted fading in and out of one or more masks.

It can also be advantageous for a region in the display to be provided for illustrating an assignment of the markings to the characteristic definitions. Alternatively, or in addition thereto, a function may also be provided, which for example displays an overlay with the meaning of the marking(s) when needed, when requested by the user or whenever the cursor reaches a marked region on the monitor.

The method according to at least one embodiment of the invention can be implemented in a particularly expedient fashion by directly accessing the command structure of a graphics card in order to display the markings, more particularly by directly executing graphic objects on a graphics card in order to display the markings.

The scope of at least one embodiment of the invention also comprises a computer system, more particularly a CT or CTA system, comprising at least one storage medium for computer programs and data, at least one visual output device, and at least one input device, wherein computer programs are stored in the storage medium and execute the method steps of the method, illustrated here, according to at least one embodiment of the invention during operation.

BRIEF DESCRIPTION OF THE DRAWINGS

In the following text, embodiments of the invention will be described in more detail with the aid of the figures, with only features required for understanding the invention being illustrated. The following reference signs are used in the process: 1 to 8: method steps; 9: vessel structure; 10: lesion; 11: stenosis; 12: mask; 13: mask; 14: rendering of an anatomical structure; 15: spherical marking, 61: C-arm system; 62: X-ray tube of the C-arm system; 63: detector of the C-arm system; 64: contrast-agent application system of the C-arm system; 66: swivel-arm drive of the C-arm system; 67: swivel arm of the C-arm system; 68: patient couch of the C-arm system; 69: control and computational unit of the C-arm system; 71: CT system; 72: X-ray tube of the CT system; 73: detector of the CT system; 74: second X-ray tube of the CT system; 75: second detector of the CT system; 76: gantry housing of the CT system; 77: contrast-agent applicator of the CT system; 78: examination couch of the CT system; 79: system axis of the CT system; B: observer; LC: encoding the lesions; P: patient; $Prg_1$ to $Prg_n$: computer programs; C: encoding; D: findings; M: mask; R: reconstruction; S: segmentation; a: probability of a voxel being part of a specific lesion.

In detail:

FIG. 2: shows an example for encoding a lesion by a CAD system;

FIG. 3: shows an example for encoding a stenosis by a CAD system;

FIG. 5: shows an example of a rendering according to an embodiment of the invention of a heart, with segmented vessels and transparent markings at the positions of positive findings, and including an enlarged detailed illustration;

DETAILED DESCRIPTION OF THE EXAMPLE EMBODIMENTS

Figure 1:
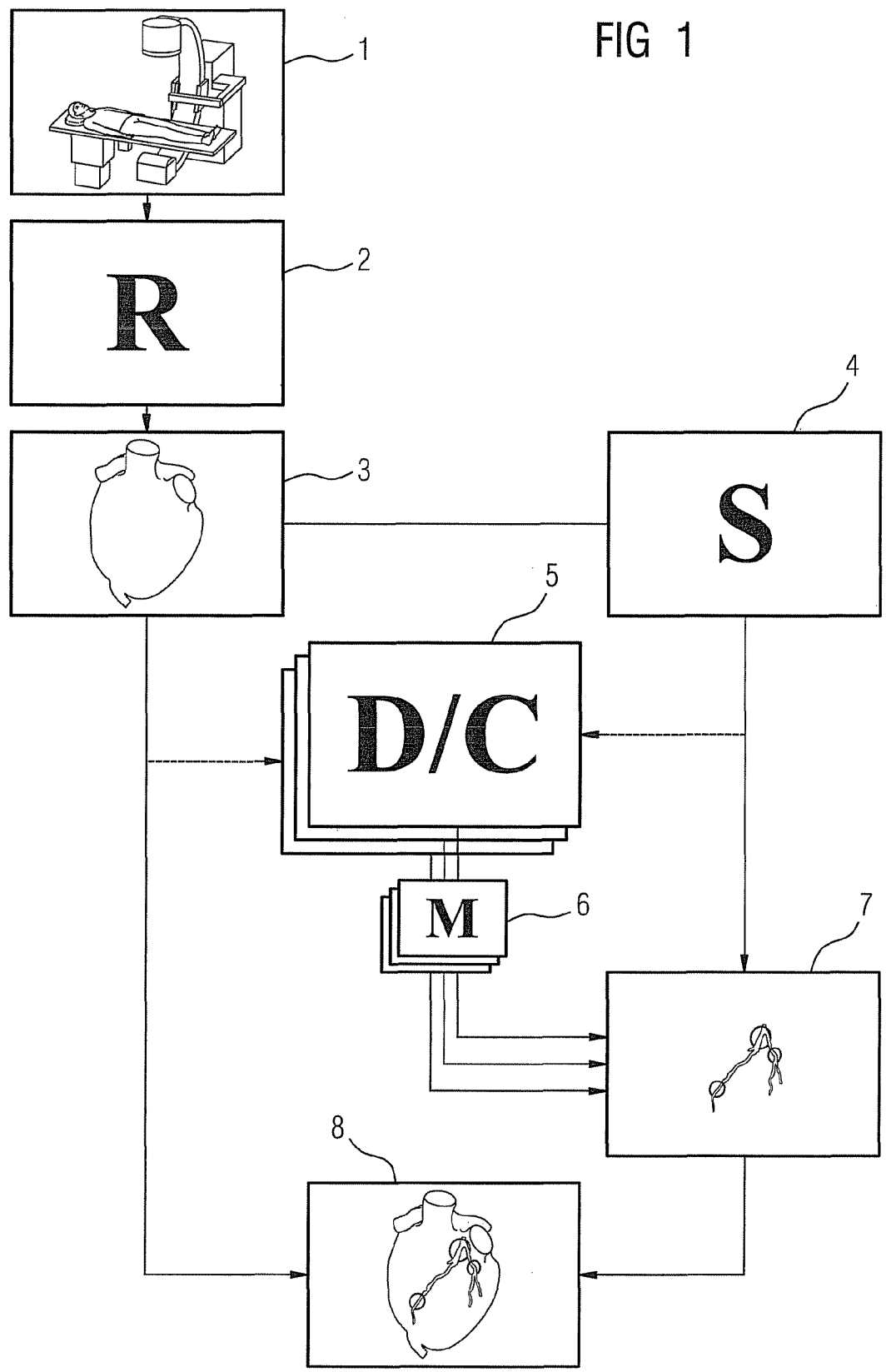
FIG. 1: shows a schematic illustration of the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The method according to an embodiment of the invention is shown in an exemplary fashion in a schematic illustration in FIG. 1. According to this, a rotating scan of a patient, usually with contrast agent being administered, is first of all performed in method step 1 with the aid of a CTA system, for example a C-arm scanner. In principle, reference should be made here to the fact that the provision of the raw data obtained during such a scan, or even finished volume data, is sufficient for the method according to the invention. In the next method step 2, a reconstruction R is performed using the measured absorption values from the scan, at least with respect to the region or volume of interest. Any method from the prior art can be used for this purpose. In method step 3, a three-dimensional CT rendering is then calculated from the volume data record obtained in this fashion, and possibly stored in a storage medium. These reconstructed data records can first of all be continued to be used at a later stage, and/or they can be sent to other locations and different users, from which or by whom findings data is respectively returned in a reply. The vessels are segmented S in method step 4 on the basis of the volume data record using methods known per se.

Entries from manual or automated findings D can now be carried out by a CAD system in method step 5 on the basis of the segmented volume data and/or else from the CT renderings from method step 3. At least the findings results, if necessary the findings sources, the findings probabilities or other relevant information as well, are furthermore encoded C into characteristic vectors in method step 5. In method step 6, the encoded data is then plotted on one or more dimensioned mask(s) M corresponding to the volume data record in terms of its dimension, or corresponding to the segmented data record. In the process, a defined region of the position of an identified lesion or anomaly in the vessel structure is provided with graphical attributes. By superposing the masks onto the volume data record of the vessel structure from method step 4, this vessel structure can now be depicted together with a transparent marking, that is to say an overlay with the previously defined mask, in method step 7. This already brings about symbolic marking of examined anomalies at this point, wherein the actual vessel structure can still be assessed by the observer despite markings due to the markings being transparent, and covered regions are not created in the process.

It is emphasized with respect to this method step 5 that the entries undertaken here, more particularly the masks from method step 6 generated from this, can be introduced into the present method from various locations and by various examining users using at least one electronic communication device. It is likewise within the scope of the invention for the generated data from method steps 1 to 4 to be transmitted to external locations at any stage and to be continued to be processed there.

Within the further course of the method, the segmented vessel structure, including the markings, can still be combined with the preferably rendered volume data record of the heart and can be displayed together as a three-dimensional rendering in method step 8, for example on a monitor.

FIG. 2 schematically shows the encoding C of a lesion 10 in a schematically illustrated vessel structure 9. In this process, the characteristic of the respective voxel is plotted on the mask 12, which is only illustrated two-dimensionally in this case but has the same dimensions as the data record of the vessel structure 9. In the present example, a distinction is made between:

☐ I = irrelevant,

▧ II = part of the vessel, and

▨ III = part of a lesion.

FIG. 3 schematically shows an example for encoding C a stenosis 11 in a schematically illustrated vessel structure 9. Here too, the characteristic of the respective voxel is plotted on the mask 13, which is likewise only illustrated two-dimensionally in this case but has the same dimensions as the data record of the vessel structure 9. The encoding C, performed automatically here by a CAD system, makes a distinction between the following characteristics:

☐ I = irrelevant,
▧ II = part of the vessel,
▣ IV = high probability,
▨ V = average probability, and
⊠ VI = low probability.

A spherical marking 15 can be identified in the mask 12 and 13, respectively, in both FIG. 2 and FIG. 3, which spherical marking encompasses the region of the discovered lesion or anomaly.

In order to obtain adequate highlighting of the discovered lesions without falsifying the anatomical representation, the diagnosis information is added in an unobtrusive fashion. Since the associated information in respect of the clinical findings was encoded as a sphere around the target anatomy, highlighting is achieved by using an adequate transmission function for displaying the region with the diagnostic information. This procedure is once again illustrated in a schematic fashion in FIG. 4. Here, the encoded values of this sphere are interpolated with the image values of the anatomical rendering. Accordingly, the boundaries of the sphere are interpolated toward higher values than the values in the interior of the region, and so the observer B obtains the spatial impression of an opaque sphere. Thus, accordingly, a transmission function assigns a low opacity to higher values of the encoded information.

Figure 4:
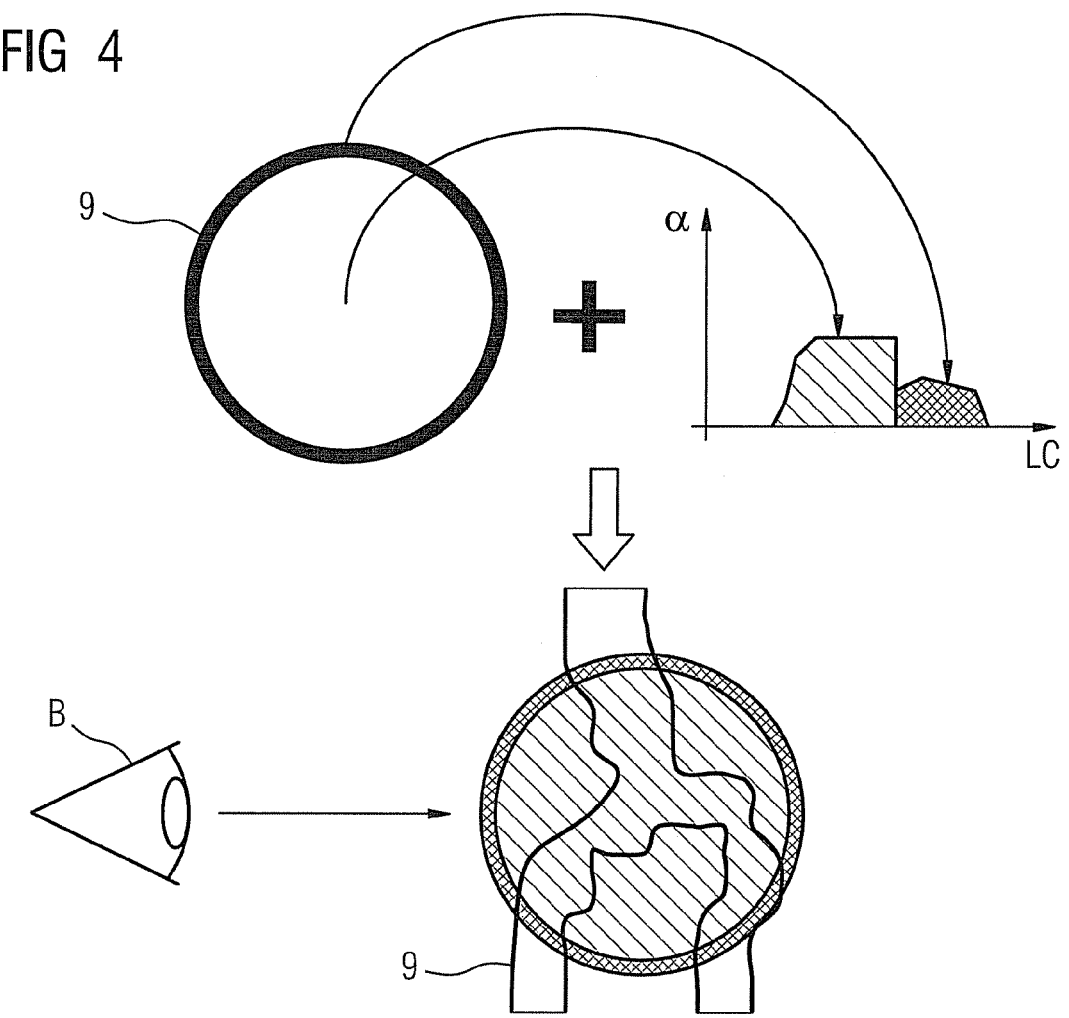
FIG. 4: shows a schematic illustration of a lesion being highlighted by volume rendering.

Advantageously, the lower values from the inner part of the region can thus have a more opaque red color in FIG. 4, whereas the boundaries of the region have a more transparent green color. This results in a "halo" effect because light beams running through the center of the region are dominated by the more opaque red color whereas light beams running through the boundaries of the region are dominated by the more transparent green.

As a result, the masks, illustrated above, with the values of the characteristic vectors can now generate an image display, which, as illustrated in FIG. 5, shows a rendering 14 of an anatomical structure, in this case a heart, which is crisscrossed by a segmented structure of the vessels. Here transparent spherical markings can be seen at relevant positions and correspond to the result of the findings in respect of the vessel structure at this location. According to an embodiment of the invention, these markings can for example be transparent spherical spheres, but finding-specific spatial representations, which surround the examined region, can also be selected. Selecting the color intensity or, possibly, the color of the marking itself can visualize the probability of the presence of a specified finding as well. However, the colors can preferably also describe the source of the findings.

In FIG. 5, a total of three positions of the segmented cardiac vessels 9 have been provided with markings 15. A detail A has been extracted for an improved illustration, in which a branching of the cardiac vessels 9 is shown in an enlarged fashion, with a lesion being highlighted at the branching by a transparent spherical marking 15. What emerges from this figure in an easily identifiable fashion is that, firstly, this marking according to an embodiment of the invention does not adversely affect the view of the observer on the relevant vessel structure of the heart and the heart itself and, secondly, this type of marking also allows a very quick and intuitive identification of the findings situation without having to spend much time reading findings written in text and without having to understand the latter.

The above-described method can be carried out in conjunction with any CT system permitting a segmentation of blood vessels. By way of example, FIG. 6 shows a C-arm system and FIG. 7 shows a CT system with a gantry and two emitter-detector systems for carrying out a dual-energy scan and/or a cardiac scan with a high time resolution.

Figure 6:
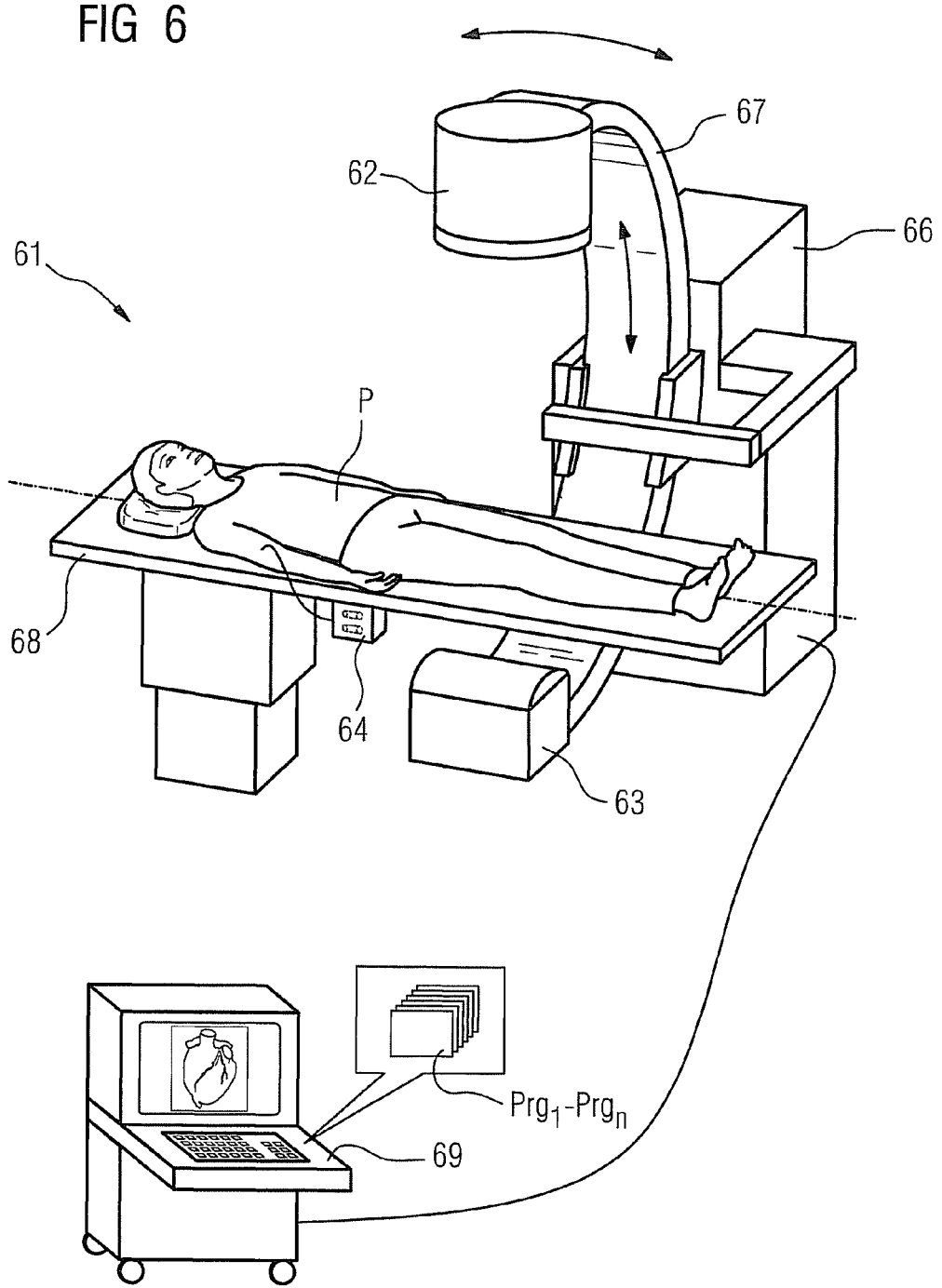
FIG. 6: shows a CTA system for carrying out the method according to an embodiment of the invention.

FIG. 6 shows a C-arm system 61, which can be used to generate CTA recordings in particular. The C-arm system 61 illustrated here comprises an X-ray tube 62 with an opposing areal detector 63. Both systems can be swiveled to any position around the patient P with the aid of a swivel-arm drive 66 and a swivel arm 67 (the C-arm). In the process, the patient P is situated on a patient couch 68, which additionally comprises a contrast-agent application system 64 for injecting a contrast agent where necessary in order to display blood vessels. The system is controlled by a control and computational unit 69, which has in its storage medium computer programs $Prg_1$ to $Prg_n$ that also execute the method for image processing according to an embodiment of the invention during operation. In particular, this control and computational unit 69 can also display the recorded region in an inventive fashion. What is not shown in the present figure, but is present in most cases, is a connection of the C-arm system to communication lines, by means of which the acquired data can be transmitted to other computer systems and users, or from which findings data, preferably in the form of masks with the same dimensions as the recordings, can be received.

Figure 7:
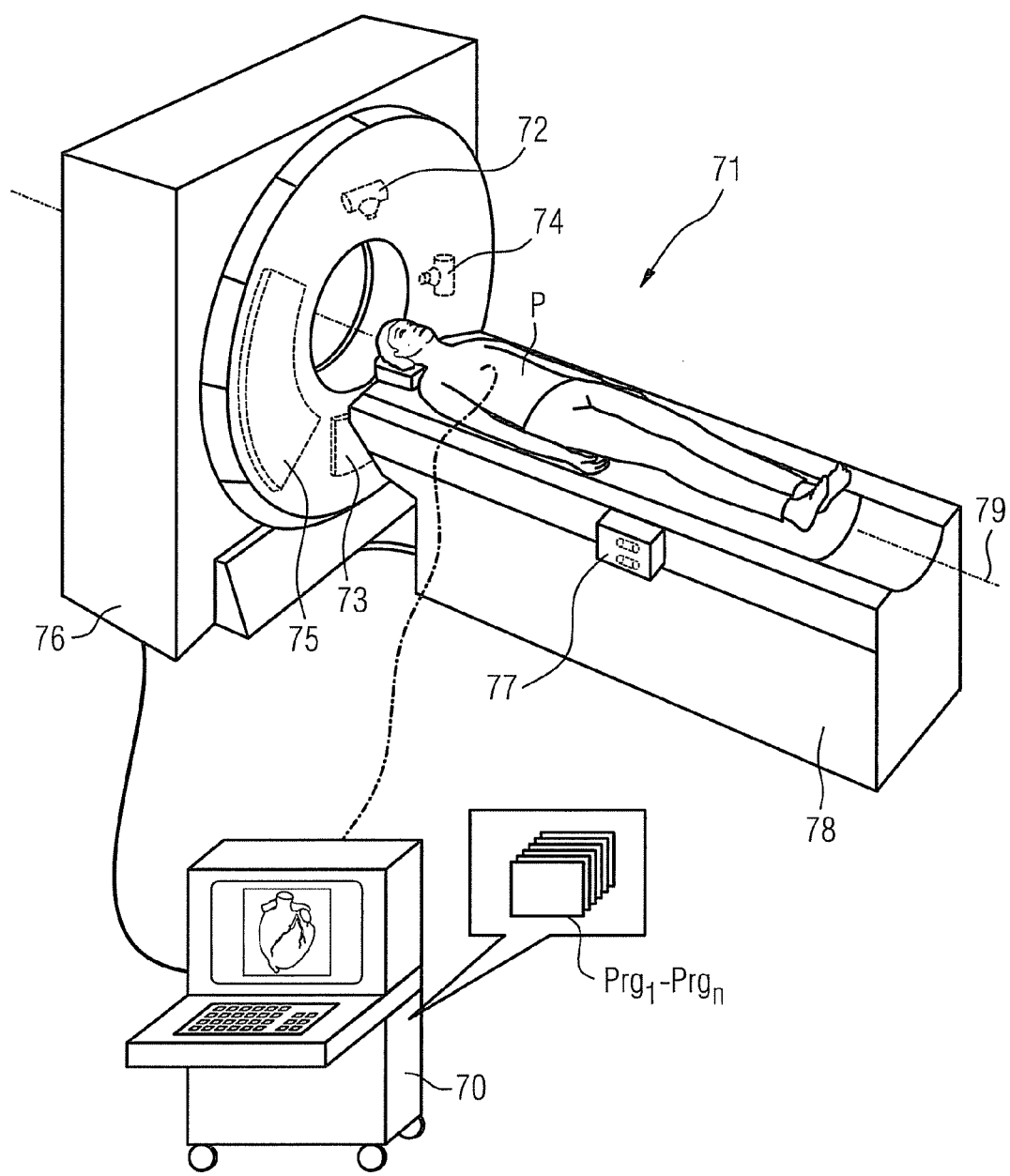
FIG. 7: shows a CT system for carrying out the method according to an embodiment of the invention.

Another embodiment of a CT system 71 that can be used within the scope of an embodiment of the invention is shown in FIG. 7. This CT system 71 has a first tube/detector system with an X-ray tube 72 and an opposing detector 73. Furthermore, this CT system 71 can optionally comprise a second X-ray tube with an opposing second detector 75. Both tube/detector systems are on a gantry, which is arranged in a gantry housing and rotates about a system axis 79 during a scan. The patient P is on a displaceable examination couch 78, which is pushed, either continuously or sequentially along the system axis 79, through the scan field located in the gantry housing 76, wherein the attenuation of the X-ray radiation emitted by the X-ray tubes is measured by the detectors.

A contrast agent bolus can be injected into the patient P during the measurement with the aid of a contrast-agent applicator 77, and so blood vessels can be identified more easily and are easier to segment. In cardiac measurements, the cardiac activity can additionally be measured with the aid of an EKG line (illustrated here by a dashed line) and an EKG-gated scan can be performed.

The CT system is controlled with the aid of a control and computational unit 70, in which there are computer programs $Prg_1$ to $Prg_n$ that can also execute the previously described method according to an embodiment of the invention. Accordingly, image data with appropriate markings can also be output by this control and computational unit 70.

This figure does not show a connection, which is present in most cases, of the CT system to communication lines either, by means of which the acquired data can be transmitted to other computer systems and users. It goes without saying that this communication path also allows the reception of findings data, preferably in the form of masks with the same dimensions as the recordings, from very different sources.

Thus, overall the method according to an embodiment of the invention presents the possibility of a very clear option for differentiating markings in findings data, which does not cover the anatomical rendering and allows a better and faster overview over a multiplicity of findings information from a multiplicity of sources.

it is understood that the aforementioned features of an embodiment of the invention can be used not only in the respective combinations specified above, without departing from the scope of an embodiment of the invention. In particular, the feature combinations described below appear to be particularly expedient:

I. A method for highlighting local characteristics in anatomical volume renderings of vessel structures, comprising the following method steps:
a. determining or receiving a volume of interest (VOI);
b. generating or receiving at least a first tomographic volume data record in the VOI, having a rendered display of a vessel structure,
c. generating or receiving at least a second volume data record, which is used as a mask for the first volume data record and has at least one characteristic vector with a minimum data width of 2 bit for each voxel,
d. accepting at least one characteristic definition for at least one predefined position or predefined region of the mask or the first volume data record, which is at the same position, and encoding the at least one characteristic definition in at least one characteristic vector of the mask,
e. combined rendering of the first volume data record and the mask, wherein the mask translucently marks a defined surrounding area of the predefined position as a function of the characteristic vectors present there.

II. The method of combination I, wherein the at least one first tomographic volume data record originates from a CT examination.

III. The method of combination I, wherein the at least one first tomographic volume data record originates from a CTA examination.

IV. The method of combinations I to II, wherein the at least one first tomographic volume data record shows the coronary arteries in the heart of a patient.

V. The method of combinations I to IV, wherein at least one entry of a characteristic definition is a finding by a medical practitioner.

VI. The method of combinations I to V, wherein at least one entry of a characteristic definition is a finding from an automated findings system.

VII. The method of combination VI, wherein the entered characteristic definition also specifies a probability of the finding being correct in addition to the finding.

VIII. The method of combinations I to VII, wherein each characteristic definition is assigned its own color and/or color intensity.

IX. The method of combinations I to VIII, wherein each probability for the presence of a finding is assigned its own color.

X. The method of combinations I to VIII, wherein each probability for the presence of a finding is assigned its own color intensity.

XI. The method of combinations I to X, wherein each user who enters a finding is assigned their own color.

XII. The method of combinations I to XI, wherein each finding is assigned its own type of illustration.

XIII. The method of combinations I to XII, wherein masks are created from at least two different sources with characteristic definitions and the at least two masks are rendered together in conjunction with the first volume data record.

XIV. The method of combinations I to XIII, wherein provision is made for one or more masks to fade in and fade out.

XV. The method of combinations I to XIV, wherein a region or a function in the display is provided for illustrating an assignment of the markings to the characteristic definitions.

XVI. The method of combinations I to XV, wherein the command structure of a graphics card is accessed directly in order to display the markings.

XVI. The method of combinations I to XV, wherein graphic objects are executed directly on a graphics card in order to display the markings.

XVIII. A computer system, more particularly a CT or CTA system, comprising:
a. a storage medium for computer programs and data,
b. at least one visual output device, and
c. at least one input device,
wherein
d. computer programs are stored, which execute the method steps of one of the preceding feature combinations during operation.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
   determining or receiving a volume of interest (VOI);
   generating or receiving at least one first tomographic volume data record in the VOI, having a rendered display of a vessel structure;
   generating or receiving at least one second volume data record, useable as a mask for the first volume data record and including at least one characteristic vector with a minimum data width of 2 bit for each voxel;
   accepting at least one characteristic definition for at least one position or region of the mask or the first volume data record, which is at the same position, and encoding the at least one characteristic definition in at least one characteristic vector of the mask; and
   combined rendering the first volume data record and the mask, wherein the mask translucently marks a defined surrounding area of the position as a function of the characteristic vectors present at the position.

2. The method as claimed in the preceding patent claim 1, wherein the at least one first tomographic volume data record shows the coronary arteries in the heart of a patient.

3. The method as claimed in claim 1, wherein at least one entry of a characteristic definition is a finding by a medical practitioner.

4. The method as claimed in claim 1, wherein at least one entry of a characteristic definition is a finding from an automated findings system.

5. The method as claimed in claim 4, wherein the entered characteristic definition also specifies a probability of the finding being correct in addition to the finding.

6. The method as claimed in claim 1, wherein masks are created from at least two different sources with characteristic definitions and the at least two masks are rendered together in conjunction with the first volume data record.

7. The method as claimed in claim 1, wherein a region or a function in the display is provided for illustrating an assignment of the markings to the characteristic definitions.

8. The method as claimed in claim 1, wherein a command structure of a graphics card is accessed directly in order to display the markings.

9. The method as claimed in claim 1, wherein graphic objects are executed directly on a graphics card in order to display the markings.

10. A computer system, comprising:
    a storage medium to store computer programs and data;
    at least one visual output device; and
    at least one input device, the stored computer programs being useable, when executed, to
      determine or receive a volume of interest (VOI);
      generate or receive at least one first tomographic volume data record in the VOI, having a rendered display of a vessel structure;
      generate or receive at least one second volume data record, useable as a mask for the first volume data record and including at least one characteristic vector with a minimum data width of 2 bit for each voxel;
      accept at least one characteristic definition for at least one position or region of the mask or the first volume data record, which is at the same position, and encode the at least one characteristic definition in at least one characteristic vector of the mask; and
      combined render the first volume data record and the mask, wherein the mask translucently marks a defined surrounding area of the position as a function of the characteristic vectors present at the position.

11. The method as claimed in claim 1, wherein the method is for highlighting local characteristics in anatomical volume renderings from CT or CTA examinations.

12. The method as claimed in claim 2, wherein at least one entry of a characteristic definition is a finding by a medical practitioner.

13. The computer system as claimed in claim 10, wherein the computer system is a CT system or CTA system.

14. A non-transitory computer readable medium including program segments for, when executed on a computer device, causing the computer device to implement the method of claim 1.

* * * * *